United States Patent [19]

Ishida et al.

[11] Patent Number: 4,721,714

[45] Date of Patent: Jan. 26, 1988

[54] ANTI-VERTIGO DRUG

[75] Inventors: Ryuichi Ishida, Suita; Yukitsuka Kudo, Kyoto, both of Japan

[73] Assignee: Tanabe Seiyaku Co., Ltd., Osaka, Japan

[21] Appl. No.: 878,602

[22] Filed: Jun. 26, 1986

[30] Foreign Application Priority Data

Jul. 12, 1985 [JP] Japan .................. 69-154932

[51] Int. Cl.$^4$ ................. A61K 31/505; A61V 31/505
[52] U.S. Cl. .................................... 514/258; 514/259
[58] Field of Search ............................... 514/258, 259

[56] References Cited

PUBLICATIONS

The Japanese Journal Of Pharmacology, vol. 40, 1986, Supplementum, p. 189P.

Japan J. Pharmacol. 32, 427–438 (1982), (Chem. Abst., 97, 4959s), pp. 427–438.
Chem. Abst. (100)–29,262F–1984.
Chem. Abst (97)–49597S–1982.

Primary Examiner—Stanley J. Friedman
Attorney, Agent, or Firm—Birch, Stewart, Kolasch & Birch

[57] ABSTRACT

An anti-vertigo drug which comprises as an active ingredient 6-amino-2-fluoromethyl-3-(o-tolyl)-4(3H)-quinazolinone (Afloqualone) or a pharmaceutically acceptable acid addition salt thereof, which is effective for the prophylaxis and treatment of vertigo and also such various symptoms accompanied with an abnormality in the reflex system of vestibulo-equilibrium sense as desesthesia of motion and position, nystagmus, dysequilibrium, head deviation, nausea, vomiting, sweating, salivation and tachycardia.

7 Claims, No Drawings

ANTI-VERTIGO DRUG

This invention relates to a new anti-vertigo drug containing as an active ingredient 6-amino-2-fluoromethyl-3-(o-tolyl)-4(3H)-quinozolinone or a pharmaceutically acceptable acid addition salt thereof.

PRIOR ART

It is known that vertigo is an abnormality of integration mechanisms of information in the central nervous system resulting from rapid dysfunction of equilibrium nervous system occurring in a vestibular nervous system and it is accompanied with various symptoms such as desesthesia of motion and position, nystagmus, dysequilibrium, head deviation, nausea, vomiting, sweating, salivation and tachycardia.

For the prophylaxis and treatment of the vertigo, there have been proposed various drugs, such as anticholinergic drugs, tranquiilizers, anti-histaminics, sedatives, vasodilators (e.g. cinnarizine, etc.), and antiemetics (e.g. diphenidol, etc.).

BRIEF SUMMARY OF THE INVENTION

The present inventors have intensively studied to improve anti-vertigo drugs and have now found that 6-amino-2-fluoromethyl-3-(o-tolyl)-4(3H)-quinazolinone (hereinafter referred to as "Afloqualone") or a pharmaceutically acceptable acid addition salt is useful as an anti-vertigo drug, while this compound has been known, it has been used as a centrally acting muscle relaxant.

An object of the invention is to provide a novel anti-vertigo drug containing as the active ingredient, Afloqualone or a pharmaceutically acceptable acid addition salt thereof. Another object of the invention is to provide a method for prophylaxis and treatment of vertigo by administering Afloqualone or a pharmaceutically acceptable acid addition salt thereof to patients suffering from vertigo. These as well as other objects and advantages of the invention will be apparent to those skilled in the art from the following description.

DETAILED DESCRIPTION OF THE INVENTION

The anti-vertigo drug of this invention comprises as an active ingredient Afloqualone or a pharmaceutically acceptable acid addition salt thereof and exhibits excellent activity inhibiting vestibular nystagmus and hence is useful for the prophylaxis and treatment of an abnomality of the reflex system of a vestibulo-equibrium sense.

The activities of Afloqualone or a salt thereof has been confirmed by experiments.

For instance, Afloqualone was orally administered to cats (dose: 10 mg/kg) and its inhibitory effects on frequency, duration and maximum amplitude of per-rotatory nystagmus or post-rotatory nystagmus were measured 30 to 180 minutes after administration of the drug to be tested. As a result, in per-rotatory nystagmus, the frequency, duration and amplitude of nystagmus were inhibited at a maximum of about 90%, 88% and 80%, respectively. Besides, in post-rotatory nystagmus, the frequency, duration and amplitude of nystagmus were inhibited at a maximum of about 86%, 80% and 78%, respectively. Moreover, a dose of 5 mg/kg, Afloqualone could inhibited the frequency and duration of per-rotatory nustagmus at a maximum of about 62% and 56%, respectively and further inhibited the amplitude of post-rotatory nystagmus at a maximum of about 52%.

In view of the action on sleep-awakefullness cycle, electroencephalogical study and also action against EEG arousal response induced by a stimulation of the brain stem reticular formation, it is unlikely that the inhibition of nystagmus by Afloqualone is would be based on the lowering action of consciousness at the above-mentioned dose. Besides, as is clear from the fact that Afloqualone could inhibit vestibular nystagmus at a dose of about ¼ (5 mg/kg, p.o. in mice) of $ED_{50}$ (about 20 mg/kg, p.o. in mice) for muscular relaxation action thereof, Afloqualone shows high specificity on an equilibrium function in addition to the action in a muscle-controlling system, and hence, it can be used for prophylaxis and treatment of various symptoms such as desesthesia of motion and position, nystagmus, dysequilibrium, head deviation, nausea, vomiting, sweating, salivation and tachycardia.

Thus, Afloqualone of this invention has excellent nystagmus inhibitory activity and is useful as an anti-vertigo drug and also useful for prophylaxis and treatment of various diseases accompanied with an abnormality in the reflex system of a verstibulo-equilibrium sense.

Afloqualone can also be used in the form of a pharmaceutically acceptable acid addition salt thereof as an anti-vertigo drug. The salt includes inorganic acid addition salts such as hydrochloride, hydrobromide, sulfate, etc., and organic acid addition salts such as aromatic sulfonic acid addition salts (e.g. benzenesulfonate, toluenesulfonate, etc.) or alkylsulfonic acid addition salts (e.g. methanesulfonate, ethanesulfonate, etc.).

Afloqualone or a salt thereof can also be used in admixture with conventional pharmaceutically acceptable carriers or diluents which are suitable for oral or parenteral administration. The pharmaceutically acceptable carriers and diluents include, for example, gelatin, lactose, glucose, sodium chloride, starches, magnesium stearate, talc, vegetable oils, and the like.

The active ingredient may be used in the form of conventional pharmaceutical preparations, for instance, solid preparations such as tablets, sugar tablets, pills, capsules, and the like, and liquid preparations such as solutions, suspensions, emulsions, and the like. These preparations are usually sterilized and may further contain other conventional additives such as stabilizers, wetting agents, emulsifiers, and the like.

When Afloqualone or a salt thereof is used as an anti-vertigo drug, it can be administered by an oral route or a parenteral route (e.g. intravenous, intramuscular or subcutaneous injection). It is preferably administered orally. The dose of Afloqualone or a salt thereof may vary depending on the age, weight or condition of the patient or severity of disease, but the dose is usually in the range of 0.05 to 10 mg/kg/day, preferably 0.1 to 2 mg/kg/day.

Moreover, Afloqualone has low toxicity [the acute toxicity ($LD_{50}$): 528.0 mg/kg, p.o. in mice] and hence it is very safe as an anti-vertigo drug.

The pharmacological activities of Afloqualone or a salt thereof are illustrated by the following Experiment.

EXPERIMENT

The experiment was carried out by using cats (weighing 1.9–3.5 kg, one group: 4–6 animals) to which a cannula was inserted into the trachea under ether anesthesia.

The cats were fixed to a stereotaxic instrument which was provided on a rotatory disc. The cats were subjected to spinal transection at $L_I$ vertebral body level, and then four legs were restricted. An electrode for electronystagmogram was fixed to the skin at bridge of nose and outer canthus. Two hours after cessation of ether anesthesia, the rotatory disc was rotated horizontally and clockwise at 30 r.p.m. (at an equal angle speed of 180°/second) for 40 seconds, by which vestibular nystagmus was induced. The diagram of vestibular nystagmus was recorded via a medical telemeter system. During the rotation, the eyes of the cats were covered.

The nystagmus was induced at an interval of 30 minutes, and after the third induction, a solution or a suspension of a test compound in 0.5% carboxymethyl cellulose solution was orally administered. In the control group, 0.5% carboxymethyl cellulose solution was administered instead of the test compound.

Based on the diagram thus obtained, the frequency, duration and the maximum amplitude of per-rotatory nystagmus and post-rotatory nystagmus were calculated.

The anti-vertigo activity of the test compound is shown by the inhibitory ratio to the ratio of the control group; which is calculated by the following equations.

$$\text{Inhibitory ratio of frequency of nystagmus} = \left[1 - \frac{\text{Frequency of nystagmus (average) in test compound-administering group}}{\text{Frequency of nystagmus (average) in control group}}\right] \times 100$$

$$\text{Inhibitory ratio of duration of nystagmus} = \left[1 - \frac{\text{Duration of nystagmus (average) in test compound-administering group}}{\text{Duration of nystagmus (average) in control group}}\right] \times 100$$

$$\text{Inhibitory ratio of maximum amplitude of nystagmus} = \left[1 - \frac{\text{Maximum amplitude of nystagmus (average) in test compound-administering group}}{\text{Maximum amplitude of nystagmus in control group}}\right] \times 100$$

The results are shown in the following Tables 1 to 3.

TABLE 1-(1)

(Inhibition of frequency of per-rotatory nystagmus)
(Inhibitory ratio: %)

| Time (minute) | Afloqualone Dose | | Diphenidol HCl* Dose |
|---|---|---|---|
| | 5 mg/kg | 10 mg/kg | 20 mg/kg |
| 30 | 49.6 | 71.5 | −18.9 |
| 60 | 49.2 | 93.4 | 6.4 |
| 90 | 61.9 | 91.5 | 1.2 |
| 120 | 45.1 | 81.7 | −2.2 |
| 150 | 50.2 | 78.5 | −6.3 |
| 180 | 57.6 | 91.2 | 5.2 |

*Chemical Name: α, α-Diphenyl-1-piperidinebutanol hydrochloride

TABLE 1-(2)

(Inhibition of frequency of post-rotatory nystagmus)
(Inhibitory ratio: %)

| Time (minute) | Afloqualone Dose 10 mg/kg | Diphenidol HCl Dose 20 mg/kg |
|---|---|---|
| 30 | 74.9 | −2.5 |
| 60 | 86.0 | −1.3 |
| 90 | 75.3 | 2.7 |
| 120 | 76.6 | 10.6 |
| 150 | 60.7 | −20.9 |
| 180 | 78.3 | −10.3 |

TABLE 2-(1)

(Inhibition of duration of per-rotatory nystagmus)
(Inhibitory ratio: %)

| Time (minute) | Afloqualone Dose | | Diphenidol HCl Dose |
|---|---|---|---|
| | 5 mg/kg | 10 mg/kg | 20 mg/kg |
| 30 | 55.7 | 68.4 | −0.4 |
| 60 | 16.6 | 87.8 | 2.0 |
| 90 | 46.8 | 86.9 | 3.0 |
| 120 | 31.6 | 67.7 | −17.3 |
| 150 | 41.9 | 73.9 | 6.5 |
| 180 | 23.6 | 77.9 | −2.9 |

TABLE 2-(2)

(Inhibition of duration of post-rotatory nystagmus)
(Inhibitory ratio: %)

| Time (minute) | Afloqualone Dose 10 mg/kg | Diphenidol HCl Dose 20 mg/kg |
|---|---|---|
| 30 | 72.0 | −17.7 |
| 60 | 81.3 | −30.3 |
| 90 | 72.2 | −11.9 |
| 120 | 79.2 | −5.0 |
| 150 | 32.8 | −36.6 |
| 180 | 63.2 | −33.8 |

TABLE 3-(1)

(Inhibition of amplitude of per-rotatory nystagmus)
(Inhibitory ratio: %)

| Time (minute) | Afloqualone Dose 10 mg/kg | Diphenidol HCl Dose 20 mg/kg |
|---|---|---|
| 30 | 64.5 | −16.1 |
| 60 | 78.5 | −10.4 |
| 90 | 57.8 | −48.5 |
| 120 | 59.9 | −33.3 |
| 150 | 60.0 | −29.7 |
| 180 | 64.1 | −1.7 |

TABLE 3-(2)

(Inhibition of amplitude of post-rotatory nystagmus)
(Inhibitory ratio: %)

| Time (minute) | Afloqualone Dose | | Diphenidol HCl Dose |
|---|---|---|---|
| | 5 mg/kg | 10 mg/kg | 20 mg/kg |
| 30 | 52.4 | 77.9 | −6.5 |
| 60 | 50.3 | 71.6 | −11.1 |
| 90 | 46.0 | 62.9 | −22.9 |
| 120 | 8.9 | 57.0 | −20.9 |
| 150 | 11.5 | 52.7 | −24.3 |
| 180 | −1.0 | 68.9 | −39.7 |

The preparation of the invention is illustrated by the following Example.

EXAMPLE 1

Tablets are prepared by the following formulation.

| Ingredient | Part by weight |
|---|---|
| Afloqualone | 10 |
| Lactose | 50 |
| Magnesium stearate | 1 |
| Corn starch | 36 |
| Dextrin | 3 |

The above ingredients are mixed and kneaded, and then the mixture is tablet-shaped by a conventional method to give tablets (100 mg per one tablet).

What is claimed is:

1. A method for the prophylaxis and treatment of vertigo, which comprises administering to a patient suffering from vertigo a prophylactically or therapeutically effective amount of 6-amino-2-fluoromethyl-3-(o-tolyl)-4(3H)-quinazolinone or a pharmaceutically acceptable acid addition salt thereof.

2. The method of claim 1, wherein the prophylaxis and treatment of vertigo is administered by an oral route or a parental route.

3. The method of claim 2, wherein the parental route is selected from intravenous, intramuscular or subcutaneous injection.

4. The method of claim 1, wherein the salt is selected from an inorganic acid salt or an organic acid salt.

5. The method of claim 4, wherein the salt is an inorganic acid salt selected from the group consisting of hydrochloride, hydrobromide and sulfate.

6. The method of claim 4, wherein the salt is an organic acid salt selected from the group consisting of aromatic sulfonic acid salt and alkylsulfonic acid salt.

7. The method of claim 4, wherein the salt is an organic acid salt selected from the group consisting of benzenesulfonate, toluenesulfonate, methanesulfonate and ethanesulfonate.

* * * * *